(12) United States Patent
Jia et al.

(10) Patent No.: US 11,649,216 B2
(45) Date of Patent: May 16, 2023

(54) METHOD FOR PREPARING MACITENTAN AND INTERMEDIATE COMPOUND THEREOF

(71) Applicant: Seasons Biotechnology (Taizhou) Co., Ltd., Taizhou (CN)

(72) Inventors: Qiang Jia, Taizhou (CN); Chi Ma, Taizhou (CN); Zhengwei Yang, Taizhou (CN); Jinjin Yang, Taizhou (CN)

(73) Assignee: Seasons Biotechnology (Taizhou) Co., Ltd., Taizhou (CN)

( * ) Notice: Subject to any disclaimer, the term of this patent is extended or adjusted under 35 U.S.C. 154(b) by 1084 days.

(21) Appl. No.: 16/336,504

(22) PCT Filed: Sep. 20, 2017

(86) PCT No.: PCT/CN2017/102452
§ 371 (c)(1),
(2) Date: Mar. 26, 2019

(87) PCT Pub. No.: WO2018/059288
PCT Pub. Date: Apr. 5, 2018

(65) Prior Publication Data
US 2021/0300880 A1    Sep. 30, 2021

(30) Foreign Application Priority Data

Sep. 28, 2016 (CN) .......................... 201610879475.1

(51) Int. Cl.
*C07D 239/47* (2006.01)
(52) U.S. Cl.
CPC .................................. *C07D 239/47* (2013.01)
(58) Field of Classification Search
None
See application file for complete search history.

(56) References Cited

U.S. PATENT DOCUMENTS

| 4,233,294 | A | 11/1980 | Murer et al. |
| 7,094,781 | B2 * | 8/2006 | Bolli ....................... A61P 27/16 544/123 |
| 7,285,549 | B2 | 10/2007 | Bolli et al. |

FOREIGN PATENT DOCUMENTS

| CN | 1524079 | A | 8/2004 |
| CN | 104411691 | A | 3/2015 |
| CN | 104447572 | A | 3/2015 |
| CN | 105272923 | A | 1/2016 |
| WO | 02053557 | A1 | 7/2002 |

OTHER PUBLICATIONS

Bolli et al., "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist", J. Med. Chem., 2012, 55—pp. 7849-7861.

(Continued)

*Primary Examiner* — Samantha L Shterengarts
(74) *Attorney, Agent, or Firm* — RatnerPrestia

(57) ABSTRACT

The present invention relates to technical field of chemical synthesis of drugs, and provides a preparation method of Macitentan and intermediate compound thereof. Adding THF solution containing compound II and 5-bromo-2-chloropyrimidine slowly into THF solution containing base to react, or adding THF solution containing compound II and THF solution containing 5-bromo-2-chloropyrimidine slowly at the same time into THF solution containing base to react and obtain Macitentan (shown as compound I), wherein the base is selected from sodium hydride, potassium hydride, lithium hydride or lithium bis(trimethylsilyl)amide. The selectivity of the preparation method is very good, which is suitable for industrial production. The obtained product Macitentan has good quality and high yield. And the product compound II also has good quality and high yield, its HPLC purity is up to 99.0%, the content of impurity A is less than 0.20%, the content of impurity B is less than 0.25%.

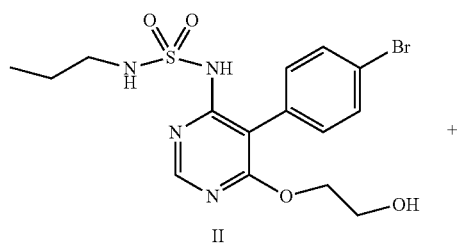

II

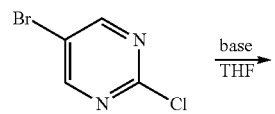

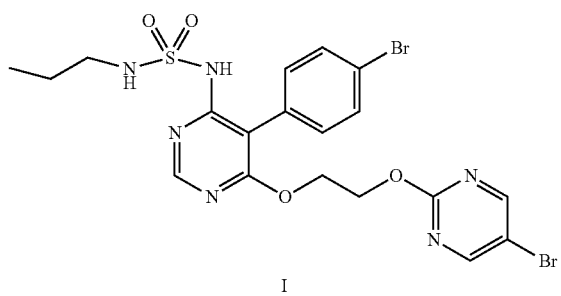

I

7 Claims, No Drawings

(56) References Cited

OTHER PUBLICATIONS

International Search Report and Written Opinion for International Application No. PCT/CN2017/102452, dated Dec. 26, 2017—7 pages.
"High Performance Liquid Chromatography", Appendix VD of "Pharmacopoeia of the People's Repbulic of China", 2010, 4 pages.
"Process for preparing N-[5-(4-bromophenyl)-6-[2-[(5-bromo-2-pyrimidinyl)oxy]ethoxyl]-4-pyrimidinyl)-N'=propylsulfamide and intermediates thereorf", IP.com Journal, 2014 , 1 (2A), 12 pages.
Chinese Office Action for Chinese Application No. 201610879475.1, dated Jul. 1, 2019 with translation, 14 pages.

* cited by examiner

METHOD FOR PREPARING MACITENTAN AND INTERMEDIATE COMPOUND THEREOF

CROSS-REFERENCE TO RELATED APPLICATION

This application is a U.S. national phase application of International Application No. PCT/CN2017/102452, filed Sep. 20, 2017, which claims the benefit of Chinese Patent Application No. CN 201610879475.1, filed on Sep. 28, 2016, the contents of each of which are incorporated herein in their entireties for all purposes.

FIELD OF THE INVENTION

The present invention relates to technical field of chemical synthesis of drugs. Specifically, it relates to a method for preparing Macitentan and intermediate compound thereof.

BACKGROUND OF THE INVENTION

Macitentan is a type of a dual endothelin receptor antagonist developed by Actelion pharmaceuticals Inc., Swiss, approved by the US Food and Drug Administration (FDA) for the treatment of adult pulmonary hypertension, under the trade name Opsumit. The chemical structural of Macitentan (compound I) is showed as follows.

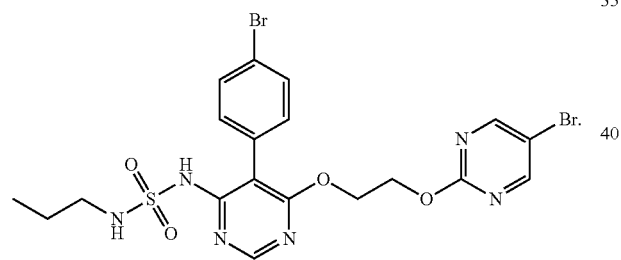

I

Martin H. Bolli et al. disclosed a general preparation method for Macitentan and published in J. Med. Chem., 2012, 55, 7849-7861. This method includes the following steps: (a) reacting compound 14 with compound 13 in dimethyl sulfoxide (DMSO) to obtain compound 15; (b) dissolving ethylene glycol in ethylene glycol dimethyl ether (DME), adding t-BuOK, raising the temperature to 40° C., stirring for 10 minutes, then adding compound 15, and reacting at 100° C. for 70 hours. Compound 16 was obtained through extraction, concentration and column chromatography purification with molar yield 86%. (c) Adding compound 16 in batches to the tetrahydrofuran (THF) suspension solution containing sodium hydride, stirring the mixture for 15 minutes, adding N,N-Dimethylformamide (DMF) to dilute the mixture, then adding 5-bromo-2-chloropyrimidine to react at 60° C. for 2 hours. Compound 17 (Macitentan) was obtained through extraction, concentration and recrystallization with molar yield 88%. The chemical reaction equation of the preparation method is as follows.

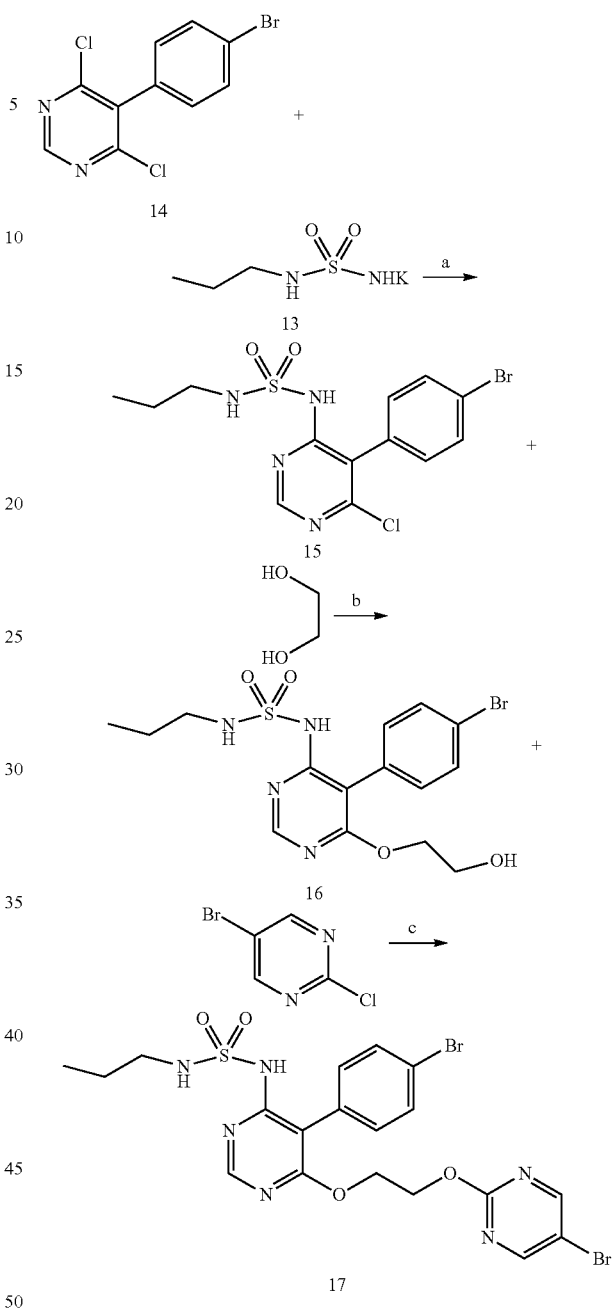

The present invention repeated the preparation method of the above mentioned literature and made analysis and detection, and found some shortcomings: the high temperature reaction time of step b is long, product needs to be purified by column chromatography, and the purity of product is low, especially the content of impurity A and impurity B is high (the chemical structure of impurity A and impurity B is shown below), which increases the by-products in the subsequent reaction. The temperature of step c is difficult to control and is not suitable for industrial production. The low solubility of compound 16 is in suspended state, which needs high-boiling point solvent DMF to dissolve, however, the solvent is harmful to environment. The use of mixture solvent increases the cost of solvent recovery and waste disposal. The purity of the product Macitentan is low, especially the content of impurity C (the chemical structure of impurity C is shown below) is high, more than 0.5%, cannot meet the quality requirements of API.

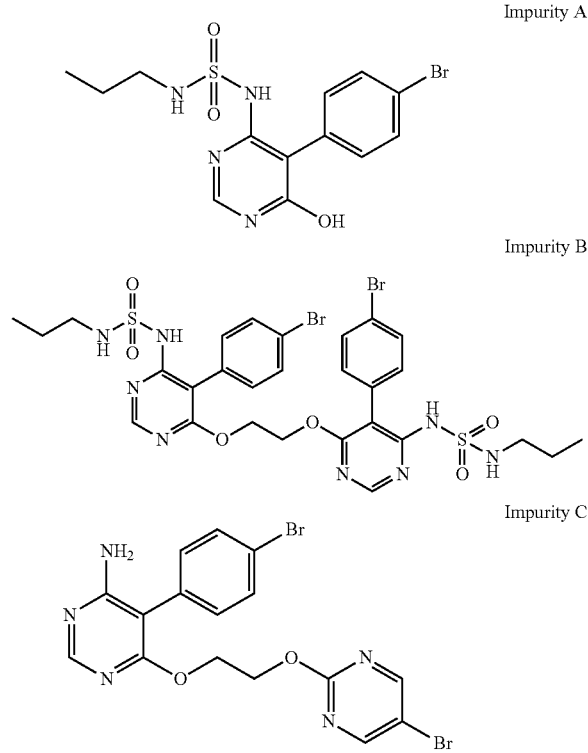

Impurity A

Impurity B

Impurity C

SUMMARY OF THE INVENTION

In view of the deficiencies of the prior art, the purpose of the present invention is to provide a novel method for preparing Macitentan. This preparation method can optimize process operation, is environmentally friendly, is suitable for industrial production, and can obtain Macitentan with high quality and high yield.

According to the purpose of the invention, the invention provides a novel method for preparing Macitentan (compound I), comprising the following steps: Adding THF solution containing compound II and 5-bromo-2-chloropyrimidine slowly into THF solution containing base to react, or adding THF solution containing compound II and THF solution containing 5-bromo-2-chloropyrimidine slowly at the same time into THF solution containing base to react and obtain Macitentan (compound I), wherein the base is selected from sodium hydride, potassium hydride, lithium hydride or lithium bis(trimethylsilyl)amide.

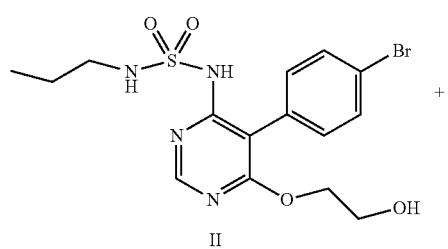

II

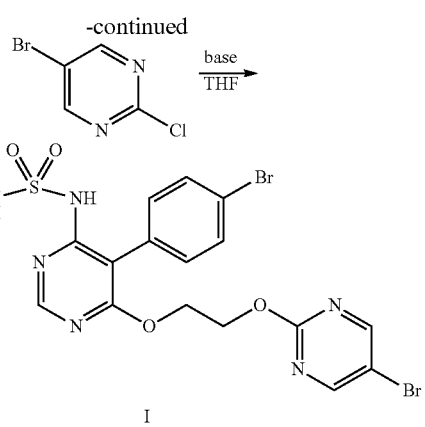

I

Preferably, the molar ratio of compound II to 5-bromo-2-chloropyrimidine is from 1:0.9 to 1:3, the molar ratio of compound II to base is from 1:2 to 1:5.

Preferably, wherein the base is sodium hydride or lithium bis(trimethylsilyl)amide.

In the preferred embodiment of this invention, the sodium hydride is the sodium hydride dispersed in mineral oil with an amount of about 60% by weight, which can be washed with or without n-heptane. Whether washing sodium hydride with n-heptane or not will not affect the reaction.

Preferably, wherein the reaction temperature is from 30° C. to 65° C.

The adding operation adopts the conventional method in this field, preferably, the adding time is from 1 hour to 8 hours.

Preferably, the reaction time is from 2 hours to 10 hours after adding.

The preparation method is carried out in the conventional stirring mode in this field.

Preferably, after the reaction is completed, add water to quench the reaction, adjust pH to 1~4 with acid, and separate; the THF phase is washed with water and layered; the THF phase is concentrated to dry, and the residue is recrystallized with solvent to obtain macitentan. The solvent used for recrystallization is preferably methanol, ethyl acetate or isopropyl acetate.

The THF solution containing compound II and 5-bromo-2-chloropyrimidine is prepared at ambient temperature. The amount of THF can be enough to make the system become solution. Commonly, the concentration of the solution is 0.5~1 times of the solubility of compound II and 5-bromo-2-chloropyrimidine in THF at ambient temperature.

The THF solution containing compound II is prepared at ambient temperature. The amount of THF can be enough to make the system become solution. Commonly, the concentration of the solution is 0.5~1 times of the solubility of compound II in THF at ambient temperature.

THF solution containing 5-bromo-2-chloropyrimidine is prepared at ambient temperature. The amount of THF can be enough to make the system become solution. Commonly, the concentration of the solution is 0.5~1 times of the solubility of 5-bromo-2-chloropyrimidine in THF at ambient temperature.

The "THF containing base" can be "THF suspension containing base" or "THF solution containing base". Wherein, the amount of THF can be used to form suspension or solution. Preferably, the ratio of the weight of base (g) to the volume of THF (ml) is from 1:5 to 1:25. In the prior art, when preparing Macitentan, compound II was firstly reacted with sodium hydride to form compound II sodium salt, and then 5-bromo-2-chloropyrimidine was added to reaction. With this adding method, when sodium hydride and compound II reacted, it would lead to intense exothermic reaction. Accumulation of large number of compound II sodium salt reacting with 5-bromo-2-chloropyrimidine violently lead to significant exothermic effect, being difficult to control temperature, easy to overheat locally and need to operate carefully. With the reaction proceeding, the concentration of compound II sodium salt and 5-bromo-2-chloropyrimidine decreased to a certain extent, the reaction rate in the later stage decreased obviously, so that the reaction did not proceed, eventually leading to the incomplete transformation of compound II and serious residual. Therefore, the reaction needed to be carried out in mixed solvent. If a single solvent (e.g. THF) was used, the reaction was heterogeneous and incomplete. The quality of the product macitentan was poor, and the purity of the HPLC was less than 99.0%, especially the content of impurity C was more than 0.5%, which cannot meet the quality requirements of APIs.

Compared with the prior art, the invention adopts the addition way of small amount and multiple batches to add compound II and 5-bromo-2-chloropyrimidine to react with base, which could control the reaction to maintain mild and stable. The addition way of small amount and multiple batches could be including continuous addition and multiple batch addition, such as adding THF solution containing compound II and 5-bromo-2-chloropyrimidine slowly; or adding THF solution containing compound II and THF solution containing 5-bromo-2-chloropyrimidine slowly at the same time; or dividing THF solution containing compound II and THF solution containing 5-bromo-2-chloropyrimidine into at least three parts respectively, then adding both of the two THF solution slowly at the same time, repeating adding until THF solution is done; or dividing THF solution containing compound II and THF solution containing 5-bromo-2-chloropyrimidine into at least three parts respectively, then adding both of the two THF solution slowly one by one, repeating adding until THF solution is done; etc. The mentioned small amount and multiple times ways are too many to list here. Various possible changes could be suggested and understood by the technician in the field and should be included in the scope of protection of the present invention. From the view point of easy operating and suitable for industrial production, preferably, adding THF solution containing compound II and 5-bromo-2-chloropyrimidine slowly into THF solution containing base, or adding THF solution containing compound II and THF solution containing 5-bromo-2-chloropyrimidine slowly into THF solution containing base at the same time.

The method for preparing Macitentan of the present invention has remarkable advantages: through improving the adding method, adding compound II and 5-bromo-2-chloropyrimidine with small amount and multiple times way to react with base, especially adding THF solution containing compound II and 5-bromo-2-chloropyrimidine slowly into THF solution containing base or adding THF solution containing compound II and THF solution containing 5-bromo-2-chloropyrimidine slowly into THF solution containing base at the same time could keep reaction mild, stable and easy to control. Adopting small amount and multiple times adding way, compound II and the base can generate compound II sodium salt (or potassium salt, lithium salt) in situ during reaction, and while 5-bromo-2-chloropyrimidine reacts with compound II sodium salt (or potassium salt, lithium salt) to generate Macitentan, which is not easy to accumulate compound II sodium salt (or potassium salt, lithium salt). It has good reaction selectivity and is suitable for industrial production. The use of single solvent THF, with nonuse of high boiling point solvent simplifies solvent recovery and waste treatment, and reduces the cost. The quality and yield of the product Macitentan are good, the purity of HPLC is over 99.80%, and the content of impurity C is less than 0.05%, which can meet the requirements for high quality of APIs.

According to the purpose of the invention, the present invention further provides a novel method for preparing compound II of Macitentan intermediate, comprising the following steps: reacting compound III with ethylene glycol in the presence of cesium carbonate to obtain compound II.

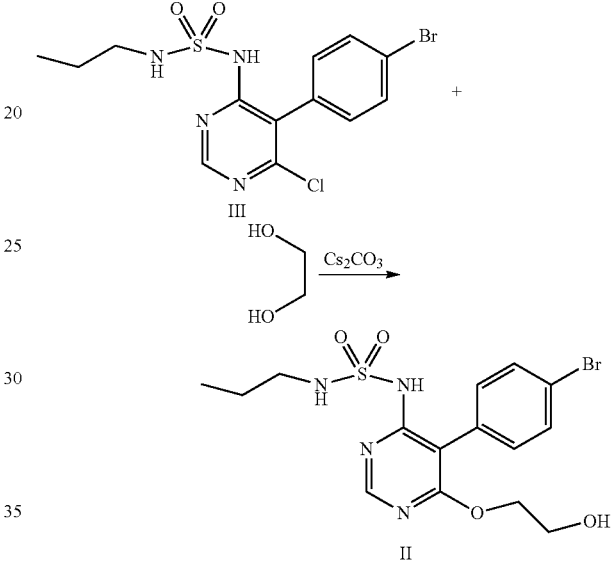

Preferably, no solvent is used in the above-mentioned method for preparing compound II.

Preferably, the molar ratio of compound III to cesium carbonate is from 1:1 to 1:5, the molar ratio of compound III to ethylene glycol is from 1:20 to 1:200; more preferably, the molar ratio of compound III to cesium carbonate is from 1:2 to 1:4, the molar ratio of compound III to ethylene glycol is from 1:40 to 1:100.

Preferably, the above-mentioned reaction temperature is from 100° C. to 150° C., more preferably, from 110° C. to 130° C.

Preferably, the above-mentioned reaction time is from 2 hours to 5 hours.

The preparation method is carried out in the conventional stirring mode in this field.

After the reaction is completed, the reaction solution is cooled to below 50° C., quenched by adding water, and adjusted to pH 2~4 with acid, then extracted, concentrated and recrystallized to get compound II. The extraction solvent could be such as ethyl acetate, recrystallization solvent could be such as methanol or isopropyl acetate, and the molar yield is 85%~92%.

In the prior art, t-BuOK was usually used as base for preparing compound II. When t-BuOK and ethylene glycol reacted, it would lead to intense exothermic reaction. Thus, t-BuOK should be added carefully. Due to the complicated operation, the temperature was not easy to control and local temperature was easy to overheat. Besides, the reaction time was as long as dozens of hours which lead to low production efficiency. Complicated column chromatograph was used to purify product in the post-treatment, which increased the cost. The purity of product compound II was low, especially the content of impurity A and impurity B was high, both were more than 0.5%.

Compared with the prior art, the method for preparing compound II of the present invention has significant advantages: Instead of t-BuOK, sodium hydride and lithium hydride or other strong base, cesium carbonate is selected to use as a base. In particular, cesium carbonate can be dissolved in ethylene glycol to form a homogeneous system. Thus, cesium carbonate can be added directly to reaction all at once, then raise temperature to react. Compared with the use of strong base such as t-BuOK which lead to severe exothermic effect needs special adding equipment, the method of the present invention simplifies the process operation and production equipment. In addition, the homogeneous reaction solves amplification effect of heterogeneous reaction, which makes the reaction mild, stable and easy to control, simple in the process operation, shortened reaction time to a few hours, and has excellent reaction selectivity, and ethylene glycol can be recycled after the reaction because of the absence of solvent. The post-treatment of reaction is simple, only conventional post-treatment methods in this field, including extraction, concentration and recrystallization, can be used to complete the separation and purification of the product with few "three wastes". The obtained product compound II has high quality and high yield. The HPLC purity of compound II is up to 99.0%, the content of impurity A is less than 0.20% and the content of impurity B is less than 0.25%. The preparation method is suitable for industrial production. As an intermediate, improving the quality of compound II is benefit to the preparation of high quality Macitentan.

In the present invention, the percentage of impurity A, impurity B or impurity C refers to its weight percentage, and HPLC purity is also calculated by the weight percentage.

In the present invention, compound III can be purchased commercially or prepared according to public literature, for example, refer to J. Med. Chem., 2012, 55, P 7858.

According to the reaction mechanism given in the above literature, compound IV reacting with alkali metal salt of compound V can obtain compound III.

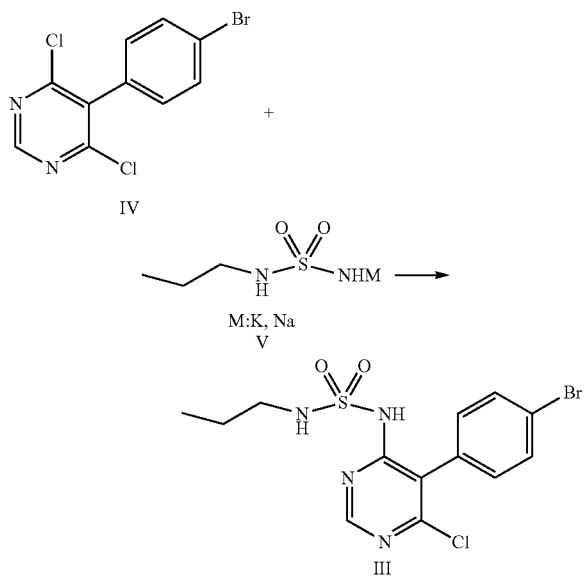

In compound V, M is selected from sodium or potassium. Sodium or potassium salt of compound V reacts with compound IV.

In one example of the invention, compound III is prepared with the following preparation method:

Using sodium salt of compound V to react with compound IV;

The molar ratio of compound IV to compound V is from 1:1 to 1:8;

The reaction solvent is polar aprotic solvent, such as DMF, DMA and DMSO;

The reaction temperature is from 50° C. to 100° C.;

The reaction time is from 2 hours to 10 hours;

After completion of the reaction, solvent is recovered by vacuum distillation, residue is quenched by water, pH value is adjusted to 6~7, then the solid is precipitated from mixture, filtered, and dried to obtain crude solid, which is recrystallized from methanol or acetonitrile to get compound III. The molar yield of compound III is up to 85%, and its HPLC purity is up to 99.0%.

The following abbreviations are used in the entire application text of the invention:
DMA: dimethylacetamide
DME: ethylene glycol dimethyl ether
DMF: N,N-Dimethylformamide
DMSO: dimethyl sulfoxide
LiHMDS: lithium bis(trimethylsilyl)amide
THF: tetrahydrofuran The beneficial effects of the invention are:
(1) The reaction process of preparing Macitentan does not easily produce the accumulation of sodium salt (or potassium salt, lithium salt) of compound II. The reaction has good selectivity and is suitable for industrial production. Product Macitentan has good quality, high yield, and its purity is up to 99.0%, the content of impurity C is less than 0.05%, which can meet the requirements of high quality of APIs.
(2) The reaction to prepare compound II is mild, stable and easy to control. The process is easy to operate, and reaction time is shortened to a few hours with excellent reaction selectivity. Besides, ethylene glycol can be recycled after completion of the reaction because of the absence of solvent. Post-treatment of the reaction is simple. Product compound II has high quality and high yield. The HPLC purity of compound II is up to 99.0%, the content of impurity A is less than 0.20% and the content of impurity B is less than 0.25%.

EXAMPLES

The following examples will further help to understand the present invention, but not be used to restrict the scope of the present invention.
(1) The reagents used in the examples are purchased commercially or self-made, and the reagents used are as follows:

Compound IV: self-made by reference to the method disclosed in patent document WO2002053557A1;

Potassium salt or sodium salt of compound V: self-made by reference to the method disclosed in literature (IP.com Journal, 2014, 14 (2A), 1-11);

Ethylene glycol: purchased from Shanghai Titan Scientific Co., Ltd.;

Cesium carbonate: purchased from Sinopharm Chemical Reagent Co., Ltd.;

Sodium hydride (60% of which is dispersed in mineral oil): purchased from Sinopharm Chemical Reagent Co., Ltd.;

5-Bromo-2-chloropyrimidine: self-made by reference to the method disclosed in patent document U.S. Pat. No. 4,233,294;

Ethyl acetate: purchased from Shanghai Titan Scientific Co., Ltd.;

N, N-Dimethylformamide: purchased from Shanghai Titan Scientific Co., Ltd.;

Methanol: purchased from Shanghai Titan Scientific Co., Ltd.;

Acetonitrile: purchased from Shanghai Titan Scientific Co., Ltd.;

Citric acid: purchased from Sinopharm Chemical Reagent Co., Ltd.;

Sodium chloride: purchased from Sinopharm Chemical Reagent Co., Ltd.;

Isopropyl acetate: purchased from Shanghai Titan Scientific Co., Ltd.;

Concentrated hydrochloric acid: purchased from Sinopharm Chemical Reagent Co., Ltd.;

Tetrahydrofuran: purchased from Shanghai Titan Scientific Co., Ltd.;

n-Heptane: purchased from Shanghai Titan Scientific Co., Ltd.;

Potassium carbonate: purchased from Sinopharm Chemical Reagent Co., Ltd.;

t-BuOK: purchased from Sinopharm Chemical Reagent Co., Ltd.;

1M of THF solution of LiHMDS: purchased from Sinopharm Chemical Reagent Co., Ltd.;

Magnesium sulfate: purchased from Sinopharm Chemical Reagent Co., Ltd.;

(2) The test instruments in the examples:

AV-400 proton nuclear magnetic resonance spectroscopy (Bruker Corporation, Germany);

LC-20AT high performance liquid chromatography (Shimadzu Corporation, Japan);

(3) The methods in the examples:

1. Compound III, compound II and compound I are tested according to the high performance liquid chromatography method in appendix VD of "Pharmacopoeia of the People's Republic of China" (2010 edition). Take appropriate amount the compounds to measure, dissolve and dilute with acetonitrile to prepare a concentration of 1.0 mg/ml as the test solution. Analysis is carried out according to the following HPLC analysis method.

HPLC method is as follows:

Column: C18 reversed-phase silica gel column;

Mobile phase A: acetonitrile:water:formic acid=49:51:0.1 (volume ratio);

Mobile phase B: acetonitrile:water:formic acid=85:15:0.1 (volume ratio);

Wavelength: 260 nm;

Flow rate: 1.0 ml/min;

Injection volume: 20 μL;

Gradient:

| Time (min) | Mobile phase A (%) | Mobile phase B (%) |
|---|---|---|
| 0 | 100 | 0 |
| 10 | 100 | 0 |
| 35 | 0 | 100 |
| 40 | 0 | 100 |
| 42 | 100 | 0 |
| 50 | 100 | 0 |

2. $^1$HNMR method is as follows:

The chemical shift (δ) is the peak of the solvent residue: chloroform protons (7.26) and TMS peaks are used as internal standards.

In the examples, room temperature refers to 10° C.~30° C.

In the examples, the chemical reaction equation of the preparation method of Macitentan is as follows:

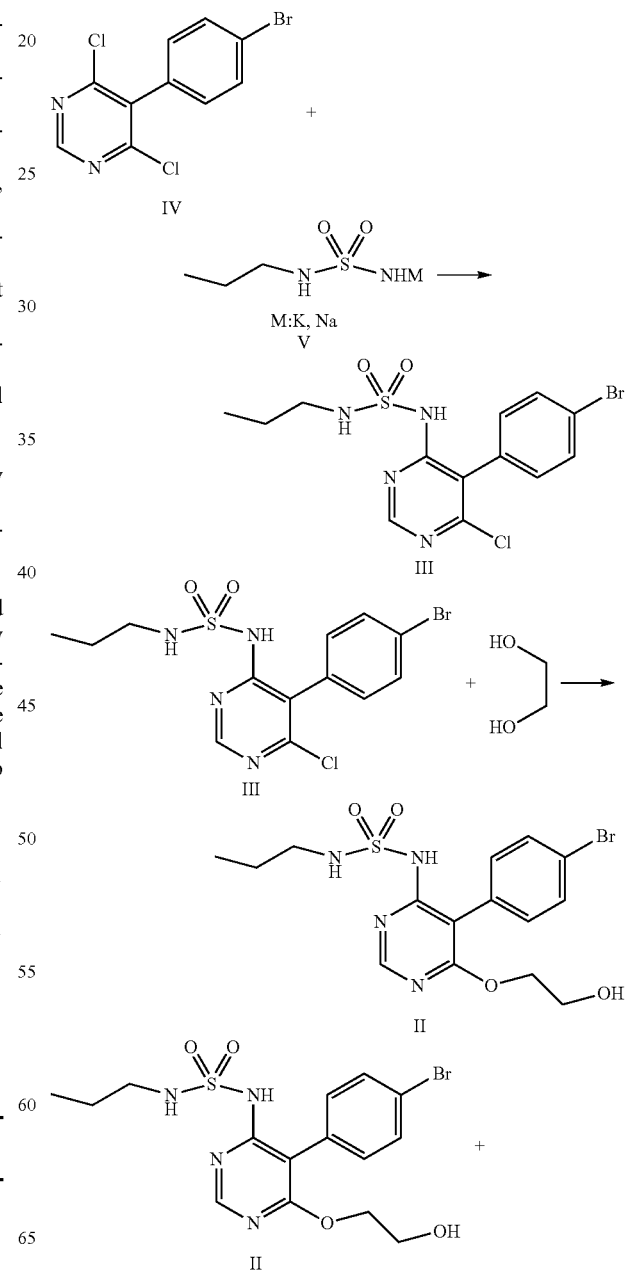

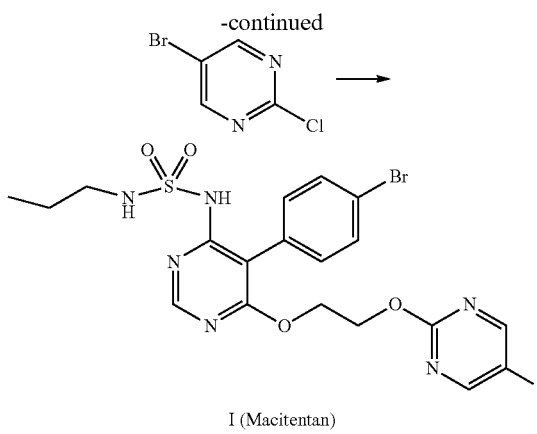

I (Macitentan)

Example 1

Preparation of Compound III 608 g (2 mol) of compound IV, 880 g (5 mol) of potassium salt of compound V and 5 L of DMF were added into a 10 L flask. Under the protection of nitrogen, the mixture was heated to 70° C., and reacted at this temperature for 4 hours, then 3.6 L of DMF is recovered by vacuum distillation. Added 3 L of water to residue, adjusted pH value to 6~7 with hydrochloric acid, then solid participated, filtered and dry to obtain crude solid, recrystallized the crude solid with 2 L of acetonitrile, finally, 700 g of white solid of compound III was obtained, the molar yield was 86%, HPLC purity was 99.7%.

$^1$HNMR data: $^1$H NMR (400 MHz, CDCl$_3$): δ 8.65 (s, 1H), 7.68-7.74 (m, 2H), 7.16-7.21 (m, 2H), 6.90 (s br, 1H), 5.52 (s br, 1H), 2.94-3.03 (m, 2H), 1.50-1.66 (m, 2H), 0.96 (t, J=7.6 Hz, 3H).

Example 2

Preparation of Compound II 40.6 g (0.1 mol) of compound III prepared from Example 1 and 250 ml of ethylene glycol were added into a 2000 ml flask, 65 g of cesium carbonate was added with stirring. Under the protection of nitrogen, the mixture was heated to 130° C., and reacted at this temperature for 5 hours, then cooled to below 50° C. Added 300 ml of water and 300 ml of ethyl acetate to the flask, adjusted pH value to 2-3 with hydrochloric acid, layered, washed the organic phase with 100 ml of water, then layered again, concentrated the organic phase to obtain the residue. The residue was recrystallized by 300 ml of isopropyl acetate and obtained 38.8 g of compound II. HPLC purity: 99.4%, content of impurity A: 0.15%, content of impurity B: 0.20%, molar yield: 90%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 3

Preparation of Compound II 40.6 g (0.1 mol) of compound III prepared from Example 1 and 500 ml of ethylene glycol were added into a 2000 ml flask, 98 g of cesium carbonate was added with stirring. Under the protection of nitrogen, the mixture was heated to 110° C., and reacted at this temperature for 4 hours, then cooled to below 50° C. Added 400 ml of water and 300 ml of ethyl acetate to the flask, adjusted pH value to 2~3 with hydrochloric acid, layered, washed the organic phase with 100 ml of water, then layered again, concentrated the organic phase to obtain the residue. The residue was recrystallized by 300 ml of methanol and obtained 39.6 g of compound II. HPLC purity: 99.5%, content of impurity A: 0.12%, content of impurity B: 0.20%, molar yield: 92%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 4

Preparation of Compound II 40.6 g (0.1 mol) of compound III prepared from Example 1 and 1100 ml of ethylene glycol were added into a 2000 ml flask, 32.6 g of cesium carbonate was added with stirring. Under the protection of nitrogen, the mixture was heated to 150° C., and reacted at this temperature for 4 hours, then cooled to below 50° C. Added 500 ml of water and 300 ml of ethyl acetate to the flask, adjusted pH value to 3~4 with 40% of aqueous solution of citric acid, layered, washed the organic phase with 100 ml of water, then layered again, concentrated the organic phase to obtain the residue. The residue was recrystallized by 200 ml of methanol and obtained 37.2 g of compound II. HPLC purity: 99.0%, content of impurity A: 0.20%, content of impurity B: 0.25%, molar yield: 86%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 5

Preparation of Compound II 40.6 g (0.1 mol) of compound III prepared from Example 1 and 500 ml of ethylene glycol were added into a 2000 ml flask, 160 g of cesium carbonate was added with stirring. Under the protection of nitrogen, the mixture was heated to 130° C., and reacted at this temperature for 2 hours, then cooled to below 50° C. Added 300 ml of water and 300 ml of ethyl acetate to the flask, adjusted pH value to 2~3 with hydrochloric acid, layered, washed the organic phase with 100 ml of water, then layered again, concentrated the organic phase to obtain the residue. The residue was recrystallized by 300 ml of methanol and obtained 37.9 g of compound II. HPLC purity: 99.4%, content of impurity A: 0.18%, content of impurity B: 0.20%, molar yield: 88%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 6

Preparation of Compound II 40.6 g (0.1 mol) of compound III prepared from Example 1 and 115 ml of ethylene glycol were added into a 1000 ml flask, 100 g of cesium carbonate was added with stirring. Under the protection of nitrogen, the mixture was heated to 100° C., and reacted at this temperature for 5 hours, then cooled to below 50° C. Added 300 ml of water and 300 ml of ethyl acetate to the flask, adjusted pH value to 2~3 with hydrochloric acid, layered, washed the organic phase with 100 ml of water, then layered again, concentrated the organic phase to obtain the residue. The residue was recrystallized by 300 ml of isopropyl acetate and obtained 37.1 g of compound II. HPLC purity: 99.4%, content of impurity A: 0.15%, content of impurity B: 0.20%, molar yield: 86%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 7

Preparation of Compound II 40.6 g (0.1 mol) of compound III prepared from Example 1 and 620 ml of ethylene glycol were added to into a 2000 ml flask, 98 g of cesium carbonate was added with stirring. Under the protection of nitrogen, the mixture was heated to 135° C., and reacted at this temperature for 4 hours, then cooled to below 50° C. Added 300 ml of water and 300 ml of ethyl acetate to the flask, adjusted pH value to 2~3 with hydrochloric acid, layered, washed the organic phase with 100 ml of water, then layered again, concentrated the organic phase to obtain the residue. The residue was recrystallized by 300 ml of isopropyl acetate and obtained 39.6 g of compound II. HPLC purity: 99.4%, content of impurity A: 0.20%, content of impurity B: 0.20%, molar yield: 92%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Example 8

Preparation of Compound I (Macitentan)

Under the protection of nitrogen, 10 g of sodium hydride (60% of which is dispersed in mineral oil) and 200 ml of THF were added into a 1000 ml flask. The mixture was heated to 45° C., and then added THF solution containing 43.1 g (0.1 mol) of compound II (compound II was prepared from Example 2), 21.3 g of 5-bromo-2-chloropyrimidine and 200 ml of THF dropwise with stirring. The adding time of the THF solution was about 3 hours, and then reacted at this temperature for 5 hours. After reaction was completed, poured the mixture to 300 ml of water to quench, and maintained the temperature below 20° C., adjusted pH value to 1-2 with hydrochloric acid, layered, washed THF phase with 100 ml of water, then layered again, concentrated THF phase to obtain residue. The residue was recrystallized by 500 ml of methanol and obtained 52.3 g of compound I (Macitentan). HPLC purity: 99.85%, content of impurity C: 0.02%, molar yield: 89%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 9

Preparation of Compound I (Macitentan)

Under the protection of nitrogen, 12 g of sodium hydride (60% of which is dispersed in mineral oil) and 200 ml of THF were added into a 1000 ml flask. The mixture was heated to 50° C., and added THF solution containing 43.1 g (0.1 mol) of compound II (compound II was prepared from Example 3), 29.1 g of 5-bromo-2-chloropyrimidine and 200 ml of THF dropwise with stirring. The adding time of the THF solution was about 1 hour, and then reacted at this temperature for 10 hours. After reaction was completed, poured the mixture to 300 ml of water to quench reaction, and maintained the temperature below 20° C., adjusted pH value to 3~4 with 30% of aqueous solution of citric acid, layered, washed THF phase with 100 ml of saturated NaCl solution, then layered again, concentrated THF phase to obtain residue. The residue was recrystallized by 150 ml of ethyl acetate and obtained 53.5 g of compound I (Macitentan). HPLC purity: 99.80%, content of impurity C: 0.04%, molar yield: 91%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 10

Preparation of Compound I (Macitentan)

Under the protection of nitrogen, 20 g of sodium hydride (60% of which is dispersed in mineral oil) and 200 ml of THF were added into a 1000 ml flask. The mixture was heated to 35° C., and added THF solution containing 43.1 g (0.1 mol) of compound II (compound II was prepared from Example 4), 17.4 g of 5-bromo-2-chloropyrimidine and 200 ml of THF dropwise with stirring. The adding time of the THF solution was about 8 hours, and then reacted at this temperature for 6 hours. After reaction was completed, poured the mixture to 300 ml of water to quench reaction, and maintained the temperature below 20° C., adjusted pH value to 2~3 with hydrochloric acid, layered, washed THF phase with 100 ml of water, then layered again, concentrated THF phase to obtain residue. The residue was recrystallized by 400 ml of methanol and obtained 50.0 g of compound I (Macitentan). HPLC purity: 99.80%, content of impurity C: 0.05%, molar yield: 85%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 11

Preparation of Compound I (Macitentan)

Under the protection of nitrogen, 8 g of sodium hydride (60% of which is dispersed in mineral oil) and 200 ml of THF were added into a 1000 ml flask. The mixture was heated to 65° C., and added THF solution containing 43.1 g (0.1 mol) of compound II (compound II was prepared from Example 5), 58 g of 5-bromo-2-chloropyrimidine and 300 ml of THF dropwise with stirring. The adding time of the THF solution was about 2 hours, and then reacted at this temperature for 3 hours. After reaction was completed, poured the mixture to 300 ml of water to quench reaction, and maintained the temperature below 20° C., adjusted pH value to 2~3 with hydrochloric acid, layered, washed THF phase with 100 ml of water, then layered again, concentrated THF phase to obtain residue. The residue was recrystallized by 400 ml of methanol and obtained 50.6 g of compound I (Macitentan). HPLC purity: 99.85%, content of impurity C: 0.02%, molar yield: 86%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 12

Preparation of Compound I (Macitentan)

Under the protection of nitrogen, 11.2 g of sodium hydride (60% of which is dispersed in mineral oil) and 200 ml of THF were added into a 1000 ml flask. The mixture was heated to 50° C., and added THF solution containing 43.1 g (0.1 mol) of compound II (compound II was prepared from Example 6), 25.3 g of 5-bromo-2-chloropyrimidine and 200 ml of THE dropwise with stirring. The adding time of the THF solution was about 3 hours, and then reacted at this temperature for 4 hours. After reaction was completed, poured the mixture to 300 ml of water to quench reaction, and maintained the temperature below 20° C., adjusted pH value to 1~2 with hydrochloric acid, layered, washed THF phase with 100 ml of water, then layered again, concentrated THF phase to obtain residue. The residue was recrystallized by 500 ml of methanol and obtained 52.9 g of compound I (Macitentan). HPLC purity: 99.85%, content of impurity C: 0.03%, molar yield: 90%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 13

Preparation of Compound I (Macitentan)

Under the protection of nitrogen, 10 g of sodium hydride (60% of which is dispersed in mineral oil) and 200 ml of THE were added into a 1000 ml flask. The mixture was heated to 45° C., and added THE solution containing 43.1 g (0.1 mol) of compound II (compound II was prepared from Example 7), 21.3 g of 5-bromo-2-chloropyrimidine and 200 ml of THE dropwise with stirring. The adding time of the THF solution was about 5 hours, and then reacted at this temperature for 4 hours. After reaction was completed, poured the mixture to 300 ml of water to quench reaction, and maintained the temperature below 20° C., adjusted pH value to 2-3 with hydrochloric acid, layered, washed THE phase with 100 ml of water, then layered again, concentrated THE phase to obtain residue. The residue was recrystallized by 500 ml of methanol and obtained 52.3 g of compound I (Macitentan). HPLC purity: 99.80%, content of impurity C: 0.04%, molar yield: 89%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 14

Preparation of Compound I (Macitentan)

Under the protection of nitrogen, 300 ml of 1M of THF solution of LiHMDS was added into a 1000 ml flask. The mixture was heated to 50° C., and added THF solution containing 43.1 g (0.1 mol) of compound II (compound II was prepared from Example 7), 17.4 g of 5-bromo-2-chloropyrimidine and 200 ml of THE dropwise with stirring. The adding time of the THF solution was about 5 hours, and then reacted at this temperature for 6 hours. After reaction was completed, poured the mixture to 300 ml of water to quench reaction, and maintained the temperature below 20° C., adjusted pH value to 2~3 with hydrochloric acid, layered, washed THF phase with 100 ml of water, then layered again, concentrated THE phase to obtain residue. The residue was recrystallized by 350 ml of methanol and obtained 50.0 g of compound I (Macitentan). HPLC purity: 99.80%, content of impurity C: 0.03%, molar yield: 85%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Example 15

Preparation of Compound I (Macitentan)

Under the protection of nitrogen, 10 g of sodium hydride (60% of which is dispersed in mineral oil) and 200 ml of THF were added into a 1000 ml flask. The mixture was heated to 45° C., and added THF solution containing 43.1 g (0.1 mol) of compound II (compound II was prepared from Example 6) and THF solution containing 21.3 g of 5-bromo-2-chloropyrimidine dropwise at the same time with stirring. The adding time of the THF solution was about 5 hours, and then reacted at this temperature for 4 hours. After reaction was completed, poured the mixture to 300 ml of water to quench reaction, and maintained the temperature below 20° C., adjusted pH value to 2-3 with hydrochloric acid, layered, washed THF phase with 100 ml of water, then layered again, concentrated THE phase to obtain residue. The residue was recrystallized by 500 ml of methanol and obtained 52.3 g of compound I (Macitentan). HPLC purity: 99.83%, content of impurity C: 0.03%, molar yield: 89%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Comparative Example 1

Preparation of Macitentan

Step (1) Preparation of Compound II

Under the protection of nitrogen, 58.7 g of ethylene glycol was dissolved in 80 ml of ethylene glycol dimethyl ether, then 8.8 g of t-BuOK was added into the mixture. Stirred for 10 minutes, then added 10.55 g of compound III prepared from Example 1. The mixture was heated to 100° C. and reacted at this temperature for 70 hours. Then poured the mixture to 200 ml of 5% of aqueous solution of citric acid, extracted with 120 ml×2 of ethyl acetate, combined the organic phases together, dried organic phase with MgSO$_4$, filtered and concentrated to obtain crude product. The crude product was purified by column chromatography (eluent: n-heptane:ethyl acetate=1:1), and 9.65 g of compound II was obtained. HPLC purity: 97.8%, content of impurity A: 0.70%, content of impurity B: 1.20%, molar yield: 86%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Step (2) Preparation of Compound I (Macitentan)

Under the protection of nitrogen, 2.8 g of sodium hydride (60% of which is dispersed in mineral oil) and 200 ml of THF were added into a 500 ml flask. Then 10 g of compound II prepared from step (1) of Comparative Example 1 was added in batches. The mixture was stirred for 15 minutes, then white solid precipitated. 40 ml of DMF was added to dissolve the mixture and get clear solution. Then 5.4 g of 5-bromo-2-chloropyrimidine was added in batches. The reaction solution was heated to 60° C. and reacted at this temperature for 2 hours. After reaction was completed, poured the mixture to 250 ml of 10% of aqueous solution of citric acid, extracted with 300 ml×2 of ethyl acetate, combined organic phases together, washed with 200 ml×2 of water, layered, dried the organic phase with MgSO$_4$, filtered, and concentrated organic phase to obtain crude product. The crude product was recrystallized by methanol and obtained 12.0 g of compound I (Macitentan). Molar yield: 88, HPLC purity: 98.7%, content of impurity C: 0.5%, $^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Comparative Example 2

Preparation of Compound II

Under the protection of nitrogen, 40 g of compound III prepared from Example 1 and 240 ml of ethylene glycol were added into a 1000 ml flask. Cooled the mixture to 10° C. with ice-water bath, added 39 g of t-BuOK carefully in batches. The reaction was exothermic reaction, thus the speed of adding t-BuOK should be controlled to maintain the temperature of reaction system below 45° C., then the mixture was heated to 100° C. and reacted at this temperature for 16 hours. After reaction completed, cooled to 50° C., added 300 ml of ethyl acetate and 100 ml of water, adjusted pH value to 2~3 with hydrochloric acid, layered, washed the organic phase with 200 ml of water, layered again, then concentrated organic phase to recover ethyl acetate and obtained residue. The residue was recrystallized by 300 ml of isopropyl acetate, and 32 g of compound II was obtained. Molar yield: 75%, HPLC purity: 98.2%, content of impurity A: 0.7%, content of impurity B: 0.5%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

Comparative Example 3

Preparation of Compound I (Macitentan)

Under the protection of nitrogen, 12 g of sodium hydride (60% of which is dispersed in mineral oil) and 400 ml of THE were added into a 1000 ml flask. Then 43.1 g of compound II prepared from Example 3 was added in batches, hydrogen was released out, so the adding speed should be controlled to avoid rushing out materials. The mixture was stirred for 15 minutes, then white solid precipitated. Then 29.1 g of 5-bromo-2-chloropyrimidine was added in batches, and tremendous amount of heat was released. The reaction solution was heated to 40° C., and when the reaction was steady, raised the temperature to 50° C. and reacted at this temperature for 4 hours. After reaction was completed, poured the mixture to 500 ml of 10% of aqueous solution of citric acid, extracted with 900 ml×2 of ethyl acetate, combined organic phases together, washed with 400 ml×2 of water, layered, dried the organic phase with MgSO$_4$, filtered, and concentrated organic phase to obtain crude product. The crude product was recrystallized by methanol and obtained 43.2 g of compound I (Macitentan). Molar yield: 80%, HPLC purity: 98.3%, content of impurity C: 0.6%, content of compound II: 0.4%.

$^1$HNMR data: $^1$H NMR (400 MHz, CDCl$_3$): δ 8.51 (s, 2H), 8.49 (s, 1H), 7.58-7.63 (m, 2H), 7.16-7.21 (m, 2H), 6.88 (s, 1H), 5.61 (t, J=6.2 Hz, 1H), 4.72-4.76 (m, 2H), 4.62-4.66 (m, 2H), 2.99 (t, J=6.8 Hz, 2H), 1.50-1.66 (m, 2H), 0.97 (t, J=7.2 Hz, 3H).

Comparative Example 4

Preparation of Compound II

Under the protection of nitrogen, 40 g of compound III prepared from Example 1 and 240 ml of ethylene glycol were added into a 1000 ml flask, then 52 g of potassium carbonate was added with stirring. Under the protection of nitrogen, the mixture was heated to 140° C. and reacted at this temperature for 24 hours. After the reaction completed, cooled to 50° C., added 300 ml of ethyl acetate and 300 ml of water, adjusted pH value to 2-3 with hydrochloric acid, layered, washed the organic phase with 200 ml of water, layered again, then concentrated organic phase to recover ethyl acetate and obtained residue. The residue was recrystallized by 300 ml of isopropyl acetate, and 30 g of compound II was obtained. Molar yield: 70%, HPLC purity: 98.1%, content of impurity A: 0.6%, content of impurity B: 0.5%.

$^1$HNMR data: $^1$H NMR (400 MHz, CDCl$_3$): δ 8.48 (s, 1H), 7.61-7.67 (m, 2H), 7.13-7.22 (m, 2H), 5.70 (s br, 1H), 4.47-4.51 (m, 2H), 3.82-3.86 (m, 2H), 2.98 (t, J=7.0 Hz, 2H), 1.50-1.66 (m, 2H), 0.95 (t, J=7.0 Hz, 3H).

The invention claimed is:
1. A method for preparing Macitentan (shown as compound I), which comprising:
   (a) adding a THF solution containing compound II and 5-bromo-2-chloropyrimidine into a THF solution containing an excess amount of a base, or
   (b) adding a THF solution containing compound II and a THF solution containing 5-bromo-2-chloropyrimidine at the same time into a THF solution containing an excess amount of a base, whereby Macitentan (shown as compound I) is produced, wherein the base is selected from sodium hydride, potassium hydride, lithium hydride or lithium bis(trimethylsilyl)amide.

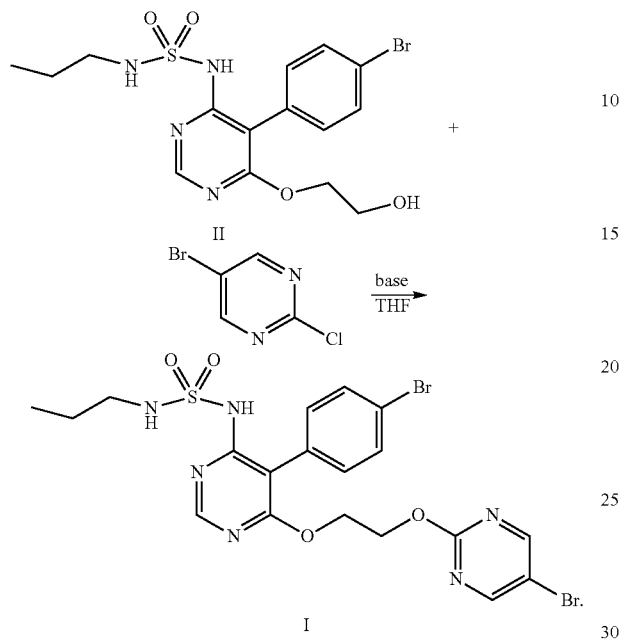

2. The method according to claim 1, wherein the molar ratio of compound II to 5-bromo-2-chloropyrimidine is from 1:0.9 to 1:3, the molar ratio of compound II to base is from 1:2 to 1:5.

3. The method according to claim 1, wherein the reaction temperature is from 30° C. to 65° C.

4. The method according to claim 1, wherein the adding time is from 1 hour to 8 hours, the reaction time after adding is from 2 hours to 10 hours.

5. The method according to claim 1, wherein the base is sodium hydride or lithium bis(trimethylsilyl)amide.

6. The method according to claim 1, wherein the adding of step (a) or (b) comprises continuous addition or multiple batch addition.

7. The method according to claim 1, wherein the compound II is prepared according to a preparation method comprising: reacting compound III with ethylene glycol in the presence of cesium carbonate to obtain compound II

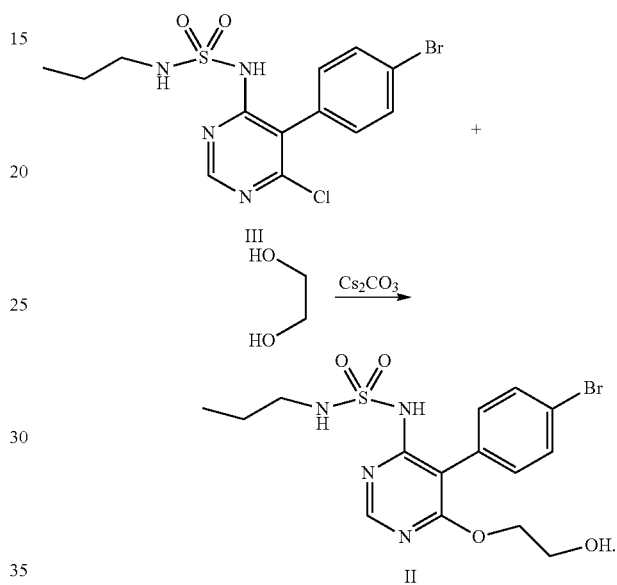

* * * * *